United States Patent [19]

Regnier et al.

[11] 4,338,323
[45] * Jul. 6, 1982

[54] PIPERIDYLBENZIMIDAZOLINONE DERIVATIVES

[75] Inventors: Gilbert Regnier, Chatenay Malabry; Alain Dhainaut, Gennevilliers; Jacques Duhault, Croissy; Michelle Boulanger, Marly-le-Roi, all of France.

[73] Assignee: Science Union et Cie, Suresnes, France

[*] Notice: The portion of the term of this patent subsequent to Apr. 28, 1998, has been disclaimed.

[21] Appl. No.: 205,725

[22] Filed: Nov. 10, 1980

[30] Foreign Application Priority Data

Nov. 15, 1979 [FR] France .................. 79 28162

[51] Int. Cl.³ .................. A61K 31/445; C07D 211/58
[52] U.S. Cl. .................. 424/266; 424/267; 546/194; 546/199
[58] Field of Search .............. 546/194, 199; 424/266, 424/267

[56] References Cited

U.S. PATENT DOCUMENTS 4,085,270  4/1978  Henschler et al. .................. 560/142
4,264,613  4/1981  Regnier et al. .................. 546/199

Primary Examiner—Henry R. Jiles
Assistant Examiner—Bernard Dentz
Attorney, Agent, or Firm—Omri M. Behr

[57] ABSTRACT

Piperidylbenzimidazolinone derivatives of the formula:

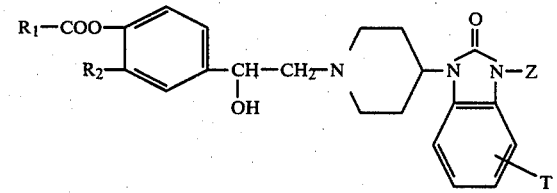

in which:
 $R_1$ is lower alkyl, phenyl, halophenyl, lower alkylphenyl, lower alkoxyphenyl, methylenedioxyphenyl, ethylenedioxyphenyl, thienyl, furyl or pyridyl.
 $R_2$ is $R'_1COO-$ or $R'_1-COO-CH_2-$ in which $R'_1$ has the same meanings as $R_1$, $R_1$ and $R'_1$ being the same or different, or $R_3NH-$ in which $R_3$ is formyl, acetyl mesyl, carbamoyl, sulfamoyl or ethoxalyl.
 Z is hydrogen, lower-alkyl or lower alkenyl, and
 T is hydrogen, lower alkyl or lower alkoxy.

These compounds and physiologically tolerable acid addition salts thereof may be used as medicines especially in the treatment of autoimmune, allergic and antiinflammatory diseases and in the treatment of dyspnea especially asthmatic and bronchial dyspnea.

9 Claims, No Drawings

PIPERIDYLBENZIMIDAZOLINONE DERIVATIVES

The present invention provides piperidylbenzimidazolinone derivatives of the formula I:

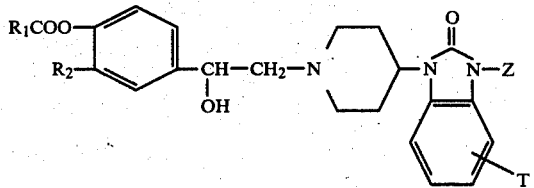

in which:

$R_1$ is selected from the group consisting of:
an alkyl radical having from 1 to 6 carbon atoms inclusive in straight and branched chain,
an unsubstituted phenyl radical and phenyl radicals mono and poly-substituted by a substituent selected from the group consisting of halogen atoms, alkyl and alkoxy radicals each having from 1 to 5 carbon atoms inclusive, methylenedioxy and ethylenedioxy radicals, and
thienyl, furyl and pyridyl radicals;

$R_2$ is selected from the group consisting of:
radicals of the formula $R'_1—COO—$ and $R'_1—COO—CH_2—$ in which $R'_1$ is a substituent selected from the meanings here-above given for $R_1$, $R_1$ and $R'_1$ being the same or different, and
a radical $R_3—NH—$ in which $R_3$ is a substituent selected from the group consisting of formyl, acetyl, mesyl, carbamoyl, sulfamoyl and ethoxalyl radicals;

Z is selected from the group consisting of a hydrogen atom, alkyl and alkenyl radicals, each having from 1 to 5 carbon atoms inclusive in straight and branched chain, and T is selected from the group consisting of a hydrogen atom, halogen atoms, and alkyl and alkoxy radicals each having from 1 to 5 carbon atoms inclusive, in straight and branched chain.

In here-above definitions, there may be mentioned for example as halogen atoms: chlorine, bromine, and fluorine atoms, as alkyl radicals: methyl, ethyl, propyl, butyl and pentyl radicals, as alkoxy radicals: methoxy, ethoxy, propoxy, butoxy and pentyloxy radicals, and as alkenyl radicals: allyl, isopropenyl, butenyl and pentenyl radicals.

The present invention also provides acid addition salts of the compounds of the general formula I. The acid addition salts are preferably physiologically tolerable acid addition salts.

The present invention further provides a process for preparing the compounds of the general formula I which comprises reducing a compound of the general formula II:

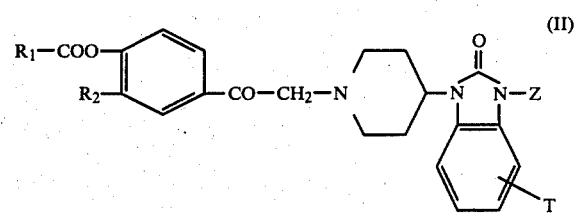

in which $R_1$, $R_2$, Z and T have the meanings given above.

The reduction of the compound II is advantageously performed with an alkali metal hydride such for example as sodium borohydride (Na BH$_4$), potassium borohydride (KBH$_4$) or sodium cyanoborohydride (Na BH$_3$ CN), in a solvent such for example as methanol, ethanol or tetrahydrofuran, in anhydrous or aqueous medium at a pH within the range of 8 to 4 according to the used reducing agent.

It is also advantageous to carry out this reduction with hydrogen at a pressure within the range of 5 to 60 bars in the presence of a catalyst containing a group VIII metal such as palladium on charcoal or platinum, in a polar solvent such for example as a water mixible aliphatic alcohol having a low boiling point, at a temperature within the range of from 25° to 80° C.

The compounds of the general formula II were prepared by esterification of compounds of the formula IIa:

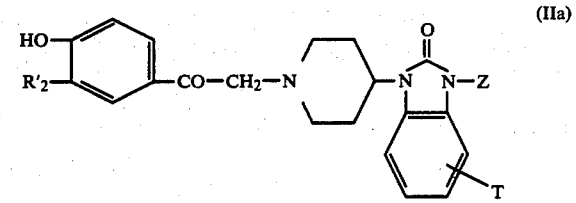

wherein Z and T have the meanings given above and $R'_2$ is selected from the group consisting of hydroxyl, hydroxymethyl or $R_3NH—$ in which $R_3$ has the meanings previously given, by the means of an acid chloride of the formula $R_1—CO—Cl$ in which $R_1$ has the meaning given above, according to methods analogous to those described by B. TULLAR and al, J. Med. Chem. 19, 834 (1976).

The compounds of the formula IIa were prepared by reacting a haloacetophenone of the general formula IIb:

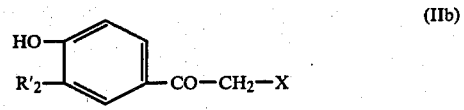

in which $R'_2$ has the meaning given above and X is selected from the group consisting of a chlorine and a bromine atom, with a piperidylbenzimidazolinone of the general formula III:

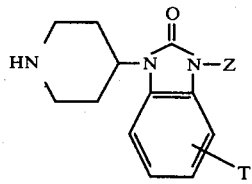 (III)

in which Z and T have the meanings given above.

Such a process is advantageously carried out by reacting the compounds IIb and III in solution in a polar solvent such for example as an aliphatic alcohol or ketone 4 or 5 carbon atoms, or dimethylformamide, at a temperature within the range of from 110° to 140° C., in the presence of an acceptor of the hydrohalide formed during the reaction. As acceptors, there may be mentioned, for example, alkali metal salts of carbonic acid, such for example as, sodium or potassium carbonate, or an excess of the piperidylbenzimidazolinone of the formula III, the excess acting as the acid acceptor.

The haloacetophenones of the general formula IIb are either known and described in literature, or prepared according to the method described by LARSEN and al, J. Med. Chem. 10,462 (1967).

1-(4-piperidyl) benzimidazolin-2-ones of the general formula III are prepared starting from the corresponding 1-(1-triphenylmethyl-4-piperidyl) benzimidazolin-2-ones.

1-(4-piperidyl) benzimidazolin-2-one is a trade product.

The present invention also provides a process for preparing compounds of the general formula I which comprises an alkylating reduction of a mixture of a piperidylbenzimidazolinone of the formula III as defined above, and a phenylglyoxal of the general formula IV:

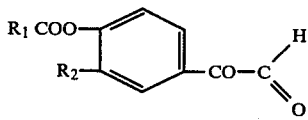 (IV)

in which $R_1$ and $R_2$ have the meanings given above.

Such an alkylating reduction is advantageously carried out, according to a method analogous to the one described by G. FODOR and al, Am. Soc. 71, 1045 (1949), by operating under a hydrogen pressure within the range of from 5 to 10 bars in the presence of a catalyst selected from VIII group metals such for example as platinum or palladium on charcoal, in a polar solvent such as a water mixible aliphatic alcohol, at a temperature within the range of from 25° to 80° C.

Phenylglyoxals of the general formula IV are prepared according to the method described by G. FODOR and al, Am. Soc. 71, 1045 (1949).

The present invention also provides a process for preparing compounds of the general formula I which comprises reacting a piperidylbenzimidazolinone of the formula III as defined above, with a halohydrin of the general formula V:

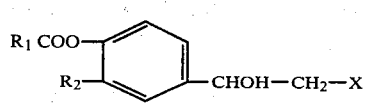 (V)

in which X, $R_1$ and $R_2$ have the meanings given above.

Such a reaction is advantageously carried out in a solvent such for example as dimethylformamide or diglyme at a temperature within the range of from 110° to 140° C., in the presence of an acceptor of the hydrohalide formed during the reaction. As acceptors, there may be mentioned for example triethylamine or an excess of the piperidylbenzimidazolinone of the formula III, the excess acting as the acid acceptor.

The starting halohydrins of the general formula V are prepared for example starting from the corresponding haloacetophenones by reducing them with an alkali metal borohydride. They are generally used in the raw state, without purification.

The compounds of the general formula I obtained according to the above processes are weak bases. Their purification is rendered particularly awkward by the presence of labile phenolic ester functions. They may therefore be purified either by chromatography on neutral alumina or by crystallization, in form of base or salt, in a polar solvent such for example as an aliphatic alcohol, acetonitrile or tetrahydrofuran.

The present invention also provides addition salts of the compounds of the general formula I with suitable mineral and organic acids, and more particularly physiologically tolerable acid addition salts. As acids which may be used for the formation of these salts there may be mentioned for example hydrochloric, hydrobromic, sulfuric, methanesulfonic and isethionic acids.

The compounds of the formula I and physiologically tolerable salts thereof possess valuable, pharmacological and therapeutic properties, especially bronchodilating, β-adrenergic and anti-allergic properties.

Their toxicity is low and their $LD_{50}$ determined in mice is higher than 800 mg/kg by oral route or higher than 100 mg/kg by intraperitoneal route, according to the compounds.

The bronchodilating activity was studied in the guinea-pig by the method of H. KONZETT and R. ROSSLER Arch. Exp. Path. U.Pharm. 195, 71 (1940). The compounds of the present invention injected intraveously at a dose within the range of from 0.05 to 1 mg/kg inhibits totally the bronchospasm caused by an intravenous administration of either histamine, serotonin or acetylcholine, and the effect of Slow Reacting Substance, at a dose within the range of from 0.100 to 0.250 mg/kg.

Submitted to the test of A. K. ARMITAGE, Brit. J. Pharmacol. 17, 196 (1961) the compounds of the present invention, administered by intra-peritoneal route at doses which vary from 0.5 to 2.5 mg/kg according to the compounds, inhibit 50% of the effect produced in the guinea-pig by an aerosol of histamine at 4%.

The compounds of the present invention administered by intra-peritoneal route at doses within the range of from 2.5 to 5 mg/kg according to the compounds, inhibit 50% of the anaphylactic shock provoked by the administration of an aerosol at 5% of albumin to guinea-pigs previously made sensitive to albumin. This test, performed for each compound to be tested on a batch of 6 guinea-pigs, was carried out as follows:

The guinea-pigs were submitted to an intra-peritoneal injection of 100 mg/kg of ovalbumin emusified in the Freund adjuvant. Four weeks later, a selection of sensitized guinea-pigs is performed as follows: the animals, fasted since the day before, are treated with an aerosol containing 5% of ovalbumin, and the times before the appearance of a deep dyspnea then pre-coma are noted. There were then selected, for the following tests, the guinea-pigs for which a deep dyspnea appears less than three minutes after the beginning of the treatment with the aerosol of ovalbumin. Eight days later, the compounds to be tested are injected by intraperitoneal route to these selected guinea-pigs fasted since the day before, then twenty minutes later these guinea-pigs are submitted to an aerosol containing 5% of ovalbumin. The times before the appearance of a deep dyspnea then pre-coma are noted and the protecting action of the tested compounds is so determined.

Furthermore, an action on the passive cutaneous anaphylaxis provoked in the rats according to Ovary's technique (Prog. Allergy 5, 459–508, S. Karger Basel/New-York), was observed when the compounds of the invention are administered by intravenous route at doses within the range of from 0.250 to 2.5 mg/kg according to the compounds.

The above pharmacological properties and the low toxicity of compounds of the general formula I and physiologically tolerable salts thereof enable their use in therapy especially in the treatment of all the diseases in which it is necessary to inhibit the antigen-antibody reactions such as autoimmune, allergic and antiinflammatory diseases and more particularly diseases in which an additional β-adrenergic effect is welcome such as asthmatic dyspnea, and chronic bronchitis.

The present invention also provides pharmaceutical compositions comprising as active ingredient a compound of the formula I or a physiologically tolerable addition salts thereof, in admixture or conjunction with a pharmaceutically suitable carrier, and especially with a carrier suitable for an administration by aerosol.

The so-obtained pharmaceutical compositions are advantageously in unit dosage forms such for example as tablets, dragees, capsules, galenic preparations suitable for sublingual administration, suppositories, injectable or drinkable solutions, or aerosols. For a guidance, the compound of example I may be used, in administration by aerosol, at doses within the range of from 250 to 1000 μg of active ingredient by puff, and by oral administration at doses within the range of from 20 to 80 mg, one to thrice a day.

The following examples illustrate the invention, the melting points being determined in a capillary tube unless otherwise stated.

EXAMPLE 1

1-[2-(3,4-bis para-toluoyloxyphenyl)-2-hydroxy]ethyl-4-(2-oxobenzimidazolin-1-yl)piperidine

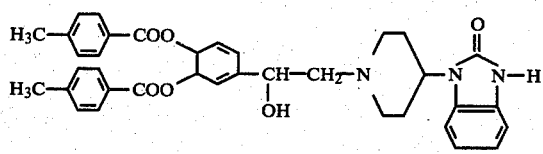

First method

A mixture of 0.38 g of sodium borohydride and 15 ml of water was added, for one hour, under stirring, to a solution of 6 g (0.01 mole) of 1-[2-(3,4-bis para-toluoyloxyphenyl)-2-oxo]ethyl-4-(2-oxobenzimidazolin-1-yl)piperidine in 200 ml of tetrahydrofuran, while the temperature was maintained to 5° C. The reactional mixture was stirred for one hour and a half at a temperature of 5° C., then it was concentrated under vacuum. The residue was taken up with 150 ml of chloroform, washed with 80 ml of an aqueous solution containing 5% of sodium bicarbonate, then thrice with each time 150 ml of water. The organic layer was dried over magnesium sulfate, then concentrated under vacuum. The residual oil, dissolved in 10 ml of ethanol acidified with a solution of hydrochloric acid in ether, crystallized to give 2 g of 1-[2-(3,4-bis para-toluoyloxyphenyl)-2-hydroxy]ethyl-4-(2-oxobenzimidazolin-1-yl)piperidine hydrochloride, M.P. 220°–226° C. (yield: 31%).

The starting 1-[2-(3,4-bis para-toluoyloxyphenyl)-2-oxo]ethyl-4-(2-oxobenzimidazolin-1-yl)piperidine, M.P. 168°–172° C. recrystallized from acetonitrile, was obtained by adding 0.16 mole of para-toluoyl chloride to a solution of 600 ml of dioxan, 0.16 mole of triethylamine and 0.04 mole of 2-[4-(2-oxobenzimidazolin-1-yl)-1-piperidyl]-3',4'-dihydroxyacetophenone, itself prepared starting from 3,4-dihydroxyphenyl chloromethylketone (trade product) and 4-(2-oxobenzimidazolin-1-yl)piperidine (trade product).

Second method

A solution of 20.15 g of 3,4-di para-toluoyloxyphenyl glyoxal, M.P. of the corresponding dinitrophenylhydrazone: 262° C. (prepared according to the technique described by C. FODOR and al. Am. Soc. 71, 1045 (1949) starting from 3,4-di paratoluoyloxyacetophenone M.P. 155°–157° C.) and 10.85 g of 4-(2-oxobenzimidazolin-1-yl)piperidine in 500 ml of ethanol at 90% was hydrogenized under 10 bars in the presence of 7.5 g of palladised charcoal containing 10% in weight of palladium. When the theoretical amount of hydrogen was absorbed, the catalyst was filtered off and the solvent evaporated under reduced pressure. The crystalline residue was stirred with twice 100 ml of boiling water in the presence of chloroform. The chloroform solution was decanted off and the solvent was evaporated under reduced pressure to give 15 g of a raw oily base. This base was dissolved in 150 ml of ethanol, and a solution of hydrochloric acid in ether was added to this ethanolic solution until the pH be 7. There were finally obtained 14.2 g of 1-[2-(3,4-bis para-toluoyloxyphenyl)-2-hydroxy]ethyl-4-(2-oxobenzimidazolin-1-yl)piperidine hydrochloride, M.P. 223°–226° C.

Third method

A solution of 10.6 g of 1-(3,4-di para-toluoyloxyphenyl)-2-chloro-1-ethanol (oil prepared starting from 3,4-di para-toluoyloxyphenyl chloromethyl ketone, M.P. 113° C., according to a method similar to O. HINSBERG, German Pat. No. 364.039 of Nov. 16, 1922) and 10.8 g of 4-(2-oxobenzimidazolin-1-yl)piperidine in 250 ml of diglyme was refluxed for 8 hours.

After the completion of the reaction, the mixture was filtered off and the solvent was evaporated under reduced pressure. The residue was taken up with twice 50 ml of boiling water in the presence of chloroform. The chloroform extract was decanted off and the solvent was evaporated under reduced pressure. The so-obtained oily residue was dissolved in 150 ml of ethanol and a solution of hydrochloric acid in ether was added to this solution until a pH of 7. There were finally obtained 8.2 g of 1-[2-(3,4-bis para-toluoyloxyphenyl)-2-hydroxy]ethyl-4-(2-oxobenzimidazolin-1-yl)piperidine hydrochloride, M.P. 220°–225° C.

EXAMPLE 2

1-[2-(3,4-trimethylacetoxyphenyl)-2-hydroxy]ethyl-4-(2-oxobenzimidazolin-1-yl)piperidine

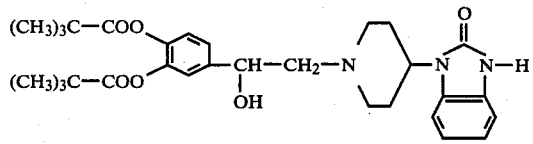

A solution of 5.72 g (0.01 mole) of 1-[2-(3,4-bis trimethylacetoxyphenyl)-2-oxo]ethyl-4-(2-oxobenzimidazolin-1-yl)piperidine hydrochloride in 120 ml of anhydrous methanol was hydrogenized for 16 hours at 60° C. under a pressure of 50 bars in the presence of 1 g of palladised charcoal containing 10% in weight of palladium. The solution was then filtered hot on celite in the presence of activated charcoal. The filter was rinsed with twice 50 ml of hot methanol. The alcoholic solution was concentrated under vacuum. The residual oil crystallized in a mixture of 8 ml of ethanol and 10 ml of petroleum ether to give 2.8 g of 1-[2-(3,4-bis trimethylacetoxyphenyl)-2-hydroxy]ethyl-4-(2-oxobenzimidazolin-1-yl)piperidine, M.P. 168° C. (yield: 50%).

The starting 1-[2-(3,4-bis trimethylacetoxyphenyl)-2-oxo]ethyl-4-(2-oxobenzimidazolin-1-yl)piperidine hydrochloride, M.P. 260°–268° C. (isopropanol) was obtained by adding 0.16 mole of pivaloyl chloride to a solution of 600 ml of dioxan, 0.16 mole of triethylamine and 0.04 mole of 2-[4-(2-oxobenzimidazolin-1-yl)-1-piperidyl]-3',4'-dihydroxyacetophenone. This last compound, the hydrochloride of which melts at 307°–313° C., was itself obtained by condensing ω-chloro-3,4-dihydroxyacetophenone with 4-(2-oxobenzimidazolin-1-yl)piperidine, in the presence of potassium carbonate in methylethyl ketone.

1-[2-(3,4-bis trimethylacetoxyphenyl)-2-hydroxy]ethyl-4-(2-oxobenzimidazolin-1-yl)piperidine, was also prepared according to the method given in Example 1, viz.

by reducing with sodium borohydride 1-[2-(3,4-bis trimethylacetoxyphenyl)-2-oxo]ethyl-4-(2-oxo-benzimidazolin-1-yl)piperidine, by an alkylating reduction of a mixture of 3,4-bis trimethylacetoxyphenylglyoxal and 4-(2-oxo-benzimidazolin-1-yl)piperidine, and by reacting 1-(3,4-bis trimethylacetoxyphenyl)-2-chloro-1-ethanol with 4-(2-oxobenzimidazolin-1-yl)piperidine.

EXAMPLES 3 TO 14

The following compounds were prepared according to the methods described in Examples 1 and 2:

(3) 1-[2-(3,4-bis para-anisoyloxyphenyl)-2-hydroxy]ethyl-4-(2-oxobenzimidazolin-1-yl)piperidine, M.P.: 137°–143° C. (methyl cyanide), starting from:
1-[2-(3,4-bis para-anisoyloxyphenyl)-2-oxo]ethyl-4-(2-oxobenzimidazolin-1-yl)piperidine, or
3,4-bis para-anisoyloxyphenylglyoxal and 4-(2-oxobenzimidazolin-1-yl)piperidine, or
1-(3,4-bis para-anisoyloxyphenyl)-2-chloro-1-ethanol and 4-(2-oxobenzimidazolin-1-yl)piperidine.

(4) 1-[2-(3,4-bis benzoyloxyphenyl)-2-hydroxy]ethyl-4-(2-oxobenzimidazolin-1-yl)piperidine, M.P. of the corresponding hydrochloride: 156° C. (ethanol), starting from:
1-[2-(3,4-bis benzoyloxyphenyl)-2-oxo]ethyl-4-(2-oxobenzimidazolin-1-yl)piperidine, M.P. 159°–163° C., or
3,4-bis benzoyloxyphenylglyoxal and 4-(2-oxobenzimidazolin-1-yl)piperidine, or
1-(3,4-bis benzoyloxyphenyl)-2-chloro-1-ethanol and 4-(2-oxobenzimidazolin-1-yl)piperidine.

(5) 1-[2-(3,4-bis ortho-toluoyloxyphenyl)-2-hydroxy]ethyl-4-(2-oxobenzimidazolin-1-yl)piperidine, M.P. of the corresponding hydrochloride: 165°–172° C. (ethanol) starting from:
1-[2-(3,4-bis ortho-toluoyloxyphenyl)-2-oxo]ethyl-4-(2-oxobenzimidazolin-1-yl)piperidine, M.P. of the corresponding hydrochloride: 224°–229° C., or
3,4-bis ortho-toluoyloxyphenylglyoxal and 4-(2-oxobenzimidazolin-1-yl)piperidine, or
1-(3,4-bis ortho-toluoyloxyphenyl)-2-chloro-1-ethanol and 4-(2-oxobenzimidazolin-1-yl)piperidine.

(6) 1-[2-(3,4-bis meta-toluoyloxyphenyl)-2-hydroxy]ethyl-4-(2-oxobenzimidazolin-1-yl)piperidine, M.P. of the corresponding hydrochloride: 186° C. (ethanol), starting from:
1-[2-(3,4-bis meta-toluoyloxyphenyl)-2-oxo]ethyl-4-(2-oxobenzimidazolin-1-yl)piperidine, M.P. of the corresponding hydrochloride: 226°–232° C., or
3,4-bis meta-toluoyloxyphenylglyoxal and 4-(2-oxobenzimidazolin-1-yl)piperidine, or
1-(3,4-bis meta-toluoyloxyphenyl)-2-chloro-1-ethanol and 4-(2-oxobenzimidazolin-1-yl)piperidine.

(7) 1-[2-(3,4-bis ortho-anisoyloxyphenyl)-2-hydroxy]ethyl-4-(2-oxobenzimidazolin-1-yl)piperidine, M.P. of the corresponding hydrochloride: 162°–171° C. (ethanol), starting from:
1-[2-(3,4-bis ortho-anysoyloxyphenyl)-2-oxo]ethyl-4-(2-oxobenzimidazolin-1-yl)piperidine, M.P. of the corresponding hydrochloride: 180° C., or
3,4-bis ortho-anisoyloxyphenylglyoxal and 4-(2-oxobenzimidazolin-1-yl)piperidine, or
1-(3,4-bis ortho-anisoyloxyphenyl)-2-chloro-1-ethanol and 4-(2-oxobenzimidazolin-1-yl)piperidine.

(8) 1-[2-(3,4-bis meta-anisoyloxyphenyl)-2-hydroxy]ethyl-4-(2-oxobenzimidazolin-1-yl)piperidine, M.P. of the corresponding hydrochloride: 154°–162° C. (methanol), starting from:
1-[2-(3,4-bis meta-anisoyloxyphenyl)-2-oxo]ethyl-4-(2-oxobenzimidazolin-1-yl)piperidine, M.P. of the corresponding hydrochloride: 210° C., or
3,4-bis meta-anisoyloxyphenylglyoxal and 4-(2-oxobenzimidazolin-1-yl)piperidine, or
1-(3,4-bis meta-anisoyloxyphenyl)-2-chloro-1-ethanol and 4-(2-oxobenzimidazolin-1-yl)piperidine.

(9) 1-[2-(3-acetoxy-4-para-toluoyloxyphenyl)-2-hydroxy]ethyl-4-(2-oxobenzimidazolin-1-yl)piperidine, starting from:
1-[2-(3-acetoxy-4-para-toluoyloxyphenyl)-2-oxo]ethyl-4-(2-oxobenzimidazolin-1-yl)piperidine, or 3-acetoxy-4-para-toluoyloxyphenylglyoxal and 4-(2-oxobenzimidazolin-1-yl)piperidine, or 1-(3-acetoxy-4-para-toluoyloxyphenyl)-2-chloro-1-ethanol and 4-(2-oxobenzimidazolin-1-yl)piperidine.

(10) 1[2-(3,4-bis para-toluoyloxyphenyl)-2-hydroxy]ethyl-4-(5-chloro-2-oxobenzimidazolin-1-yl)piperidine, M.P. of the corresponding hydrochloride: 180°-190° C. (ethanol), starting from:
1-[2-(3,4-bis para-toluoyloxyphenyl)-2-oxo]ethyl-4-(5-chloro-2-oxobenzimidazolin-1-yl)piperidine, or
3,4-bis para-toluoyloxyphenylglyoxal and 4-(5-chloro-2-oxobenzimidazolin-1-yl)piperidine, or
1-(3,4-bis para-toluoyloxyphenyl)-2-chloro-1-ethanol and 4-(5-chloro-2-oxobenzimidazolin-1-yl)piperidine.

(11) 1-{2-[3,4-bis(2,6-dimethylbenzoyloxy)phenyl]-2-hydroxy}ethyl-4-(2-oxobenzimidazolin-1-yl)piperidine, M.P. of the corresponding hydrochloride: 162°-170° C. (ethanol), starting from:
1-{2-[3,4-bis(2,6-dimethylbenzoyloxy)phenyl]-2-oxo}ethyl-4-(2-oxobenzimidazolin-1-yl)piperidine, or
3,4-bis(2,6-dimethylbenzoyloxy)phenylglyoxal and 4-(2-oxobenzimidazolin-1-yl)piperidine, or
1-[3,4-bis(2,6-dimethylbenzoyloxy)phenyl]-2-chloro-1-ethanol and 4-(2-oxobenzimidazolin-1-yl)piperidine.

(12) 1-[2-(3,4-bis piperonyloyloxyphenyl)-2-hydroxy]ethyl-4-(2-oxobenzimidazolin-1-yl)piperidine, M.P. of the corresponding hydrochloride: 196° C. (ethanol/benzene) starting from:
1-[2-(3,4-bis piperonyloyloxyphenyl)-2-oxo]ethyl-4-(2-oxobenzimidazolin-1-yl)piperidine, or
3,4-bis piperonyloyloxyphenylglyoxal and 4-(2-oxobenzimidazolin-1-yl)piperidine, or
1-(3,4-bis piperonyloyloxyphenyl)-2-chloro-1-ethanol and 4-(2-oxobenzimidazolin-1-yl)piperidine.

(13) 1-[2-(3-formylamino-4-para-toluoyloxyphenyl)-2-hydroxy]ethyl-4-(2-oxobenzimidazolin-1-yl)piperidine, starting from:
1-[2-(3-formylamino-4-para-toluoyloxyphenyl)-2-oxo]ethyl-4-(2-oxobenzimidazolin-1-yl)piperidine, or
3-formylamino-4-para-toluoyloxyphenylglyoxal and 4-(2-oxobenzimidazolin-1-yl)piperidine, or
1-(3-formylamino-4-para-toluoyloxyphenyl)-2-chloro-1-ethanol and 4-(2-oxobenzimidazolin-1-yl)piperidine.

(14) 1-[2-(3,4-bis nicotinoyloxyphenyl)-2-hydroxy]ethyl-4-(2-oxobenzimidazolin-1-yl)piperidine, starting from:
1-[2-(3,4-bis nicotinoyloxyphenyl)-2-oxo]ethyl-4-(2-oxobenzimidazolin-1-yl)piperidine, or
3,4-bis nicotinoyloxyphenylglyoxal and 4-(2-oxobenzimidazolin-1-yl)piperidine, or
1-(3,4-bis nicotinoyloxyphenyl)-2-chloro-1-ethanol and 4-(2-oxobenzimidazolin-1-yl)piperidine.

We claim:

1. A compound selected from the group consisting of: piperidylbenzimidazolinone derivatives of the formula:

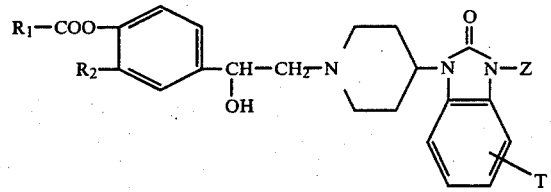

in which:
$R_1$ is selected from the group consisting of:
. alkyl having from 1 to 6 carbon atoms inclusive in straight and branched chain,
. unsubstituted phenyl and phenyl mono- and poly-substituted by a substituent selected from the group consisting of halogen, alkyl and alkoxy each having from 1 to 5 carbon atoms inclusive, methylenedioxy, and ethylenedioxy, and
. thienyl, furyl, and pyridyl;
$R_2$ is selected from the group consisting of:
. $R'_1$—COO— and $R'_1$—COO—$CH_2$— in which $R'_1$ is a substituent selected from the meanings here-above given for $R_1$, $R_1$ and $R'_1$ being the same or different, and
. $R_3$—NH— in which $R_3$ is selected from the group consisting of formyl, acetyl, mesyl, carbamoyl, sulfamoyl, and ethoxalyl;
Z is selected from the group consisting of hydrogen, alkyl, and alkenyl each having from 1 to 5 carbon atoms inclusive in straight and branched chain, and
T is selected from the group consisting of hydrogen, halogen, alkyl and alkoxy each having from 1 to 5 carbon atoms inclusive in straight and branched chain; and
physiologically tolerable acid addition salts thereof.

2. A compound of claim 1 which is 1-[2-(3,4-bis para-toluoyloxyphenyl)-2-hydroxy]ethyl-4-(2-oxobenzimidazolin-1-yl)piperidine, and its hydrochloride.

3. A compound of claim 1 which is 1-[2-(3,4-bis trimethylacetoxyphenyl)-2-hydroxy]ethyl-4-(2-oxobenzimidazolin-1-yl)piperidine, and its hydrochloride.

4. A compound of claim 1 which is 1-[2-(3,4-bis para-anisoyloxyphenyl)-2-hydroxy]ethyl-4-(2-oxobenzimidazolin-1-yl)piperidine.

5. A compound of claim 1 which is 1-[2-(3,4-bis benzoyloxyphenyl)-2-hydroxy]ethyl-4-(2-oxobenzimidazolin-1-yl)piperidine, and its hydrochloride.

6. A compound of claim 1 which is 1-[2-(3,4-bis ortho-anisoyloxyphenyl)-2-hydroxy]ethyl-4-(2-oxobenzimidazolin-1-yl)piperidine, and its hydrochloride.

7. A compound of claim 1 which is 1-[2-(3,4-bis meta-anisoyloxyphenyl)-2-hydroxy]ethyl-4-(2-oxobenzimidazolin-1-yl)piperidine, and its hydrochloride.

8. A pharmaceutical composition active as a bronchodilator containing as active ingredient between 20 and 80 milligrams per unit dose of a compound of claim 1 together with a suitable pharmaceutical carrier.

9. A method for treating a living animal body afflicted with autoimmune, allergic or antiinflammatory diseases, asthmatic dyspnea or chronic bronchitis, comprising the step of administering an amount of a compound of claim 1 which is effective for the alleviation of the said condition.

* * * * *